(12) United States Patent
Yasumoto

(10) Patent No.: US 6,593,752 B1
(45) Date of Patent: Jul. 15, 2003

(54) METHOD FOR INSPECTING HERMETICALLY SEALED PACKAGES

(75) Inventor: Kenji Yasumoto, Toyonaka (JP)

(73) Assignee: Joven Denki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/936,252

(22) PCT Filed: Feb. 21, 2000

(86) PCT No.: PCT/JP00/00985
§ 371 (c)(1),
(2), (4) Date: Sep. 7, 2001

(87) PCT Pub. No.: WO00/54038
PCT Pub. Date: Sep. 14, 2000

(30) Foreign Application Priority Data

Mar. 10, 1999 (JP) .......................................... 11-062810

(51) Int. Cl.$^7$ ................................................ G01N 27/00
(52) U.S. Cl. ........................................ 324/557; 324/558
(58) Field of Search ................................. 324/557, 501, 324/702, 703, 750–753, 558

(56) References Cited

U.S. PATENT DOCUMENTS

| | | | | |
|---|---|---|---|---|
| 4,914,395 A | * | 4/1990 | Hamada | 324/514 |
| 4,956,558 A | * | 9/1990 | Batishko et al. | 250/301 |
| 5,796,113 A | * | 8/1998 | Nagli et al. | 250/483.1 |
| 5,850,144 A | * | 12/1998 | Howells et al. | 324/557 |
| 6,087,666 A | * | 7/2000 | Huston et al. | 250/361 R |
| 6,288,554 B1 | * | 9/2001 | Yasumoto | 324/558 |

FOREIGN PATENT DOCUMENTS

| | | | | |
|---|---|---|---|---|
| GB | 144255 | * | 6/1973 | G01J/3/10 |
| JP | 50-71385 | | 6/1975 | |
| JP | 53-10485 | | 1/1978 | |
| JP | S61-239122 | | 10/1986 | |
| JP | 61-239122 | | 10/1986 | |
| JP | 6-74941 | | 3/1994 | |
| JP | 7-229948 | | 8/1995 | |
| JP | 8-240569 | | 9/1996 | |

* cited by examiner

*Primary Examiner*—N. Le
*Assistant Examiner*—John Teresinski
(74) *Attorney, Agent, or Firm*—Koda & Androlia

(57) ABSTRACT

An inspection method for inspecting a hermetricaly sealed package for pinholes in which electrically conductive contents are covered with an electrically insulating film, an electrical conductor connected to a high voltage output terminal of a DC high voltage power supply is put into contact with a side face of the hermetrically sealed package to electrify the contents. Next, a terminal of a lead wire which is grounded is put into close contact or proximity to an inspection portion of the package where pinholes are more likely to occur. Then, a discharge current derived fom the inspection objection portion that flows only when a pinhole is present is detected by discharge current detector.

5 Claims, 4 Drawing Sheets

METHOD FOR INSPECTING HERMETICALLY SEALED PACKAGES

TECHNICAL FIELD

The present invention relates to a method for inspecting completely hermetically sealed packages, such as food and medical consumption articles, for any pinholes.

BACKGROUND ART

Today, hermetically sealed packaging is used in a variety of commodities including food and medical consumption articles such as physiological saline to keep their contents in a sterilized state. In the case of food, the presence of pinholes would cause the contents of the package to contact the air, resulting in deterioration or rot. Also, in the case of medical consumption articles, for example, transfusion bottles, the presence of pinholes would cause contamination or deterioration. Thus, the pinhole inspection for these hermetically sealed packages is of great importance.

Conventionally, this pinhole inspection would be carried out in the following method. That is, because a hermetically sealed package does not allow an electrode to be penetrated thereinto, for example in the case of food, a metal pin is stuck into a completed package and taken as one electrode so as to serve as an opposed electrode to an external electrode set in contact with the package. In this state, with a high voltage applied between the two electrodes, the hermetically sealed package is inspected for pinholes, and after the inspection, any pinholes are hermetically sealed in a different process. However, this inspection method has had a drawback that the inspection process would be complicated, requiring a subsequent process of closing the pinholes.

In order that solve this drawback and to allow a pinhole inspection to be done without damaging the completed hermetically sealed package, there has been provided a method for pinhole inspection, for example, in which a food is sandwiched between a pair of electrodes and a voltage is applied a between both electrodes so as to give a large difference between capacitances that are formed between the individual electrodes and the food, respectively. Then, a current which is generated by a spark between one of the electrodes and the food is detected, by which any pinhole is detected (for example, Japanese Patent Publication SHO 50-6998).

When the presence or absence of any pinhole is detected by detecting a current generated by a spark as described above, it would be the actual case in terms of practical work that the presence or absence of pinholes is detected by a change (magnitude) of the detected current. In this case, there may arise an error to the current at the detection point due to some influence of humidity and temperature on the peripheries of the inspection object as well as floating fine dusts or the like, which is the atmosphere in the inspection. As a result, the decision as to the presence or absence of pinholes could not be free from misoperations such as a decision of the presence of a pinhole notwithstanding the absence of any pinhole.

Further, applying a high voltage between the two electrodes that sandwich the hermetically sealed package would cause potential differences to concentrate to weak portions of the electrically insulating film of the hermetically sealed package so that pinholes would be made, thus resulting in a tendency of increasing pinholes. This tendency would have an adverse effect on the inspection package, as a further problem.

The present applicant has previously applied an invention with an aim of preventing the occurrence of misoperations due to the atmosphere in the inspection. In this method, while a hermetically sealed package the contents of which, such as fluid, powder or food having electrical conductivity, are coated with an electrically insulating film is placed on a grounded support electrode of a specified configuration, a DC high voltage is applied between the support electrode and an electrode put into close contact with or opposed proximity to an inspection-object end portion of the hermetically sealed package so that the contents of the hermetically sealed package are electrically charged via a pinhole, if any, present at the inspection-object end portion. Then, the electrode put into contact with the inspection-object end portion is grounded, where a discharge current from the inspection-object end portion is detected, by which the present or absence of any pinhole of the hermetically sealed package is detected (Japanese Patent Applications Nos. HEI 8-53816 and HEI 10-158569).

Using this method has made it possible to fully prevent the occurrence of misoperations without being affected by the atmosphere in the inspection such as humidity and temperature. However, the method has still required a sequence of inspection procedure.

The present invention has been accomplished in view of these and other problems. An object of the present invention is therefore to provide an efficient method for inspecting a hermetically sealed package which method allows the inspection to be achieved with further simpler procedure, which method is fully prevented from occurrences of misoperations due to the atmosphere during the inspection, and further which method never causes pinholes to be made in the hermetically sealed package even if the electrically insulating film has weak portions.

For this method, the hermetically sealed package to be inspected can be exemplified, in the field of food, principally by cylindrical-shaped packages such as sausage hermetically sealed and packaged in unit pieces, and besides retort foods packed in a flat bag made of plastic film. In the field of medical consumption articles, the hermetically sealed package can be exemplified by blood preparations such as transfusion blood and blood plasmas contained in a plastic bag in addition to transfusion agents such as physiological saline or Ringer's solution contained in a transfusion bottle also made of plastic as the inspection object for prevention of contamination and deterioration of the contents due to contact with outside air via pinholes. High-resistance electrifiable fluids such as distilled water can also be inspected.

Furthermore, hermetically sealed packages in which a particle or powder conductive material such as cooked rice or solid-matter iron powder is hermetically sealed in a plastic bag also can be an object of inspection as well.

DISCLOSURE OF THE INVENTION

In order to achieve the above object the present invention provides a method for inspecting a hemeticauly sealed package, comprising the steps of: electrifying a hermetically sealed package 3 in which contents 1 such as electically conductive fluid or powder or food are covered with an electrically insulating film 2 by putting an electrical conductor 4 namely a single electrode of a pair of voltage output terminals of a DC high voltage power supply 6 into contact with or proximity to a side face portion $3_1$ of the hermetically sealed package 3 so that the contents 1 in the hermetically sealed package 3 are electrified; then, putting an electrode 5 connected to a grounded grounding wire 8 into proximity to or contact with a inspection-object portion 3a; and detecting occurence of light or/and noise due to electric discharge that occurs in a presence of a pinhole at the inspection-object portion 3a to thereby detect any pinhole of hermetically sealed package 3.

As a result of this, when the electrical conductor 4 derived from the voltage output terminal of the DC high voltage power supply 6 is put into contact with or proximity to the side face portion $3_1$ of the hermetically sealed package 3, the electrically conductive contents 1 in the hermetically sealed package 3 are electrified to a negative or positive potential of the DC high voltage (0.6 kV–30 kV) applied to the electrical conductor 4, causing negative (–) ions or positive (+) ions to be generated.

Next, as the electrode 5 connected to the grounded grounding wire 8, it occurs in the presence of a pinhole at the inspection-object portion 3a that if negative (–) ions are generated within the contents 1, the negative (–) ions are concentrated to the pinhole, or that if positive (+) ions are generated within the contents 1, the positive (+) ions are concentrated to the pinhole, where electric discharge occurs between the inspection-object portion 3a and the electrode 5 connected to the grounded grounding wire 8 through the pinhole. This discharge will cause light or/and noise to be generated, and the light or/and noise can be detected by the sensor 7. By this detection, it can be detected that a pinhole is present at the inspection-object portion 3a.

If no pinhole is present at the inspection-object portion 3a, there will not occur electric discharge, so that neither light or/and noise will not be generated. Accordingly, the sensor 7 will not be activated, which makes it possible to detect that no pinhole is present at the inspection-object portion 3a. In this case, an optical sensor may be used with a view to detecting light which is to be generated by the discharge, a noise sensor may be used with a view to detecting noise which is to be generated by the discharge, and both an optical sensor and a noise sensor may be used with a view to detecting both light and noise.

For the electrode 5, although various forms of electrodes suitable for the inspection-object portion 3a are possible, it is effective to employ an electrically conductive brush made of electrically conductive plastic fiber.

This electrically conductive brush as an electrode 5 may be formed of acrylic fiber impregnated with copper oxide. This electrically conductive brush employs plastic fiber as its base material, being soft in terms of rigidity so as not to damage the inspection object, lending itself to extremely advantageous use as an electrode when its brush shape is formed in accordance with the inspection object.

Also, it is advantageous that the step of detecting the presence or absence of generation of light due to electric discharge that occurs in the presence of a pinhole at the inspection-object portion 3a is a step of letting light emission due to the discharge incident on a photomultiplier tube $7_2$ via an optical fiber $7_1$ to convert the light into electricity by the photomultiplier tube $7_2$, and detecting the electricity by a detector $7_3$. By doing so, even with a weak light emission due to the discharge, the detection can easily be achieved.

In such a case, it is advantageous that the light emission due to the electric discharge is let incident on the optical fiber $7_1$ via an ultraviolet-transmitting, visible-absorption filter $7_4$. By doing so, even if the place is so bright that light is hard to detect, the light emission can easily be detected by detecting only ultraviolet rays generated by the discharge phenomenon. In addition, an optical fiber $7_1$ that allow ultraviolet rays to easily transmit therethrough should be used.

Furthermore, depending on the circumstances, the light emission due to the electric discharge may be let incident on the optical fiber $7_1$ via an ultraviolet-transmitting, visible-absorption filter $7_4$ and an ultraviolet-converting fluorescent glass $7_5$. By doing so, in the case where the inspection-object portion 3a is annular or other shaped, by using an ultraviolet-transmitting, visible-absorption filter $7_4$ and an ultraviolet-converting fluorescent glass $7_5$ both of which are so wide as to cover the annular or other shape, it becomes possible to easily capture electric discharge no matter where in the annular or other shape the electric discharge has occurred, convert only ultraviolet components of the emitted light into fluorescent light, and thus easily detect the light emission.

BRIEF DESCRIPTION OF THE DRAWINGS

FIG. 2 is an arrangement diagram showing another example in which pinhole inspection is performed by detecting light due to electric discharge after the electrification of the contents of a transfusion bottle of physiological saline or the like;

REFERENCE NUMERAL

Figure 1A:
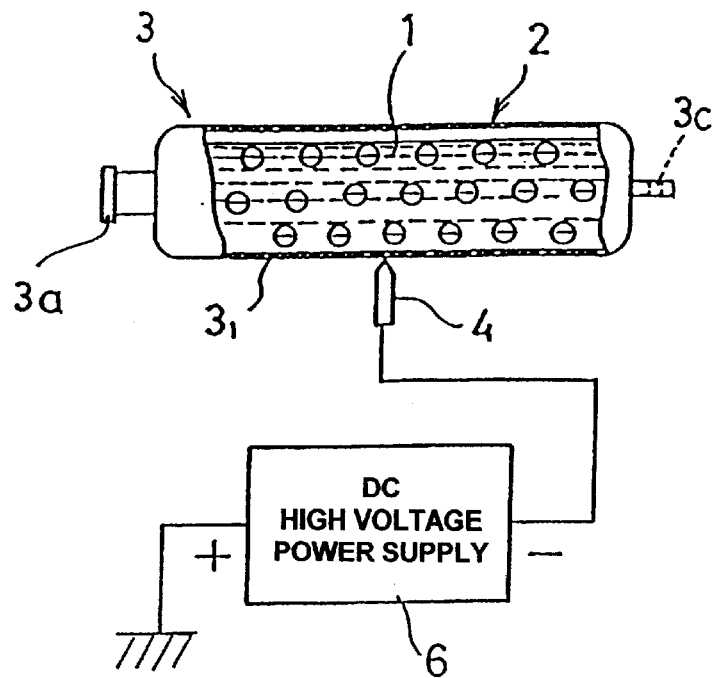
FIG. 1 is an arrangement diagram showing an example in which the inspection method of the present invention is applied to the pinhole inspection of a transfusion bottle of physiological saline or the like, where FIG. 1 (A) shows a state of electrifying the contents and FIG. 1 (B) shows a state in which the pinhole inspection is performed.

1 . . . contents, 2 . . . electrically insulating film, 3 . . . hermetically sealed package, $3_1$ . . . side face portion of hermetically sealed package, 3a . . . inspection-object portion, 5 . . . electrode, 6 . . . DC high voltage power supply, 7 . . . sensor, $7_1$ . . . optical fiber, $7_2$ . . . photomultiplier tube, $7_3$ . . . detector, $7_4$ . . . ultraviolet-transmitting, visible-absorption filter, $7_5$ . . . ultraviolet-converting fluorescent glass, 8 . . . grounding wire.

BEST MODE FOR CARRYING OUT THE INVENTION

Preferred embodiments of the present invention are described with reference to the accompanying drawings.

In the present invention, an electrically insulating film 2 with which electrically conductive contents 1 of a hermetically sealed package 3 to be inspected are covered may be plastic or plastic film or glass matching the contents.

More specifically, when the contents 1 are fish sausage as an example, a bag made of vinylidene chloride film is used. After minced meat of fish sausage is filled in the bag, the bag is clipped at both ends by aluminum wire and subjected to retort sterilization. Further, even retort foods employing a bag of composite film (laminate film) can be the objective hermetically sealed package to be inspected. In this case, bags of a composite film made of nylon and polypropylene, polyester and polypropylene, or polyester and vinylidene chloride and polypropylene are used. On the other hand, in the case of transfusions such as physiological saline and Ringer's solution, transfusion bottles of a plastic specified for individual cases are used and besides glass containers are also usable.

Furthermore, the contents 1 may also be fluids of solid matters, such as electrically conductive powder such as iron powder or other electrically conductive powders.

For supporting the hermetically sealed package 3 in order that an electrical conductor 4 is put into contact with or proximity to a side face portion $3_1$ of the hermetically sealed package 3 so as to electrify the contents 1, the support member may be of any shape, such as a planar support member (either plastic or metallic depending on the circumstances of use), a support member whose upper contact surface is planar shaped with many rollers of small diameter located adjacent to one another, or a support member having a circular-arc inner surface so that the cross section of the support member corresponds to the circular sausage or the like. An electrode 5 connected to a grounded grounding wire 8 may be a metallic one of any shape corresponding to an inspection-object portion 3a.

EXAMPLE 1

Figure 1B:
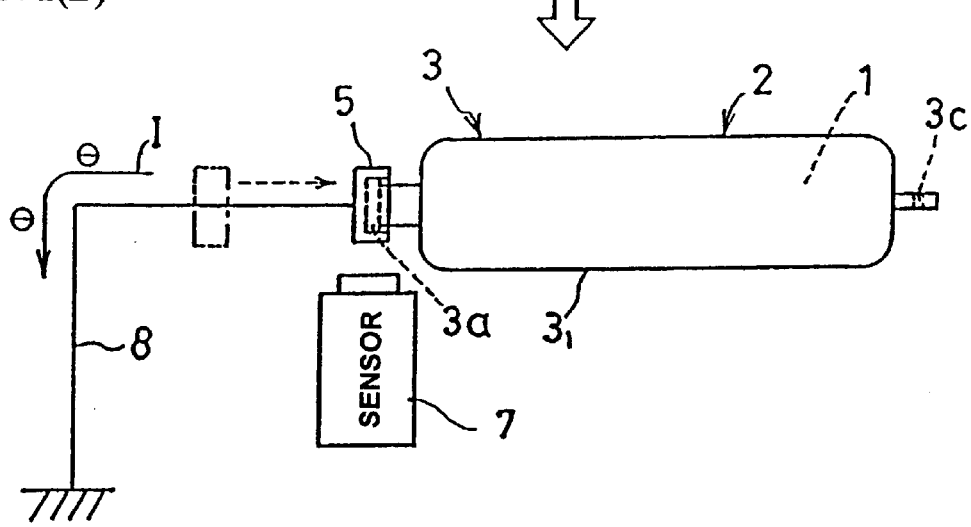

FIG. 1 shows an example in which the hermetically sealed package 3 is a transfusion bottle for use in instillation in which physiological saline or other transfusion is hermetically sealed, where the contents 1 within the hermetically sealed package 3 are electrified to detect a pinhole at the inspection-object portion 3a of the hermetically sealed package 3.

The transfusion bottle 3 has a body portion formed of a rather thick plastic film 2 with a cross section formed into a rounded 65 mm×90 mm rectangular shape having a height of 240 mm, and a content volume of 1000 milliliters. The inspection-object portion 3a where pinholes are liable to occur is one formed in such a way that an unshown rubber stopper portion for insertion of an instillation needle is provided airtight at an opening of a stepped end portion having an outer diameter of 28 mm and a thickness of 8 mm while a hanging ring portion is provided on the opposite side. Places in this inspection-object portion 3a where pinholes or gaps equivalent to pinholes are liable to occur are peripheries of the ring-shaped stepped portion at which the rubber stopper is held, and the boundary portion between the rubber stopper portion and the opening of the stepped portion at which the rubber stopper is held.

In order to inspect the inspection-object portion 3a of this transfusion bottle 3 for pinholes, with the transfusion bottle 3 placed on an arbitrary support base made of, for example, plastic (not shown), first a tip of the electrical conductor 4 connected to the negative (−) side of a DC high voltage power supply 6 whose positive (+) side is grounded is put into contact with or proximity to the side face portion $3_1$ of the transfusion bottle 3, so that the contents 1 within the transfusion bottle 3 are electrified by the negative (−) potential of the DC high voltage (0.6 kV–30 kV) applied to the electrical conductor 4 (see FIG. 1 (A)).

Also, as the electrode 5 for, in the presence of a pinhole at the inspection-object portion 3a, generating light or/and noise due to electric discharge between the electrode 5 and the inspection-object portion 3a when the electrode 5 is put into proximity to or contact with the inspection-object portion 3a, a small cup-like metallic member having a recessed portion into which the inspection-object portion 3a can be fitted is connected to a terminal end of the grounded grounding wire 8 in such a way that the metallic member can be brought into proximity to or coverage on the inspection-object portion 3a.

Thus, when the electrode 5 of the small cup-like metallic member is brought into proximity to the inspection-object portion 3a, it occurs that, in the presence of a pinhole at the inspection-object portion 3a, electric discharge is generated in the gap between the inspection-object portion 3a and the front of the electrode 5, or further that as the electrode 5 is brought into coverage on the inspection-object portion 3a, electric discharge is generated between the electrode 5 and the stepped portion of the inspection-object portion 3a, causing a discharge current I to flow through the grounding wire 8, with the result that negative (−) electric charges of the contents 1 are lost. As light or/and noise is generated at this occurrence, this light or/and noise is detected by a sensor 7. By detecting light or/and noise with this sensor 7, it can be detected whether or not a pinhole is present at the inspection-object portion 3a (see FIG. 1 (B)).

In the absence of any pinhole at the inspection-object portion 3a, electric discharge is not generated and therefore no light or/and noise is generated. Accordingly, the sensor 7 will not be activated, by which it can be detected that no pinholes are present at the inspection-object portion 3a. In addition, it can be seen in the figure that the tip of the electrical conductor 4 is brought into contact with the side face portion $3_1$ of the hermetically sealed package 3 from below. Otherwise, the tip of the electrical conductor 4 may of course be brought into contact from side horizontally, or from above vertically.

Further, with regard to the electrode 5, which is the small cup-like metallic member, a plurality of slits may also be provided in the side face of the electrode 5 so that generation of light or/and noise can easily be detected by the sensor 7 when electric discharge occurs between the inner surface of the recessed portion of the electrode 5 and the inspection-object portion 3a during the fitting-in of the inspection-object portion 3a into the recessed portion of the electrode 5.

EXAMPLE 2

Figure 2:
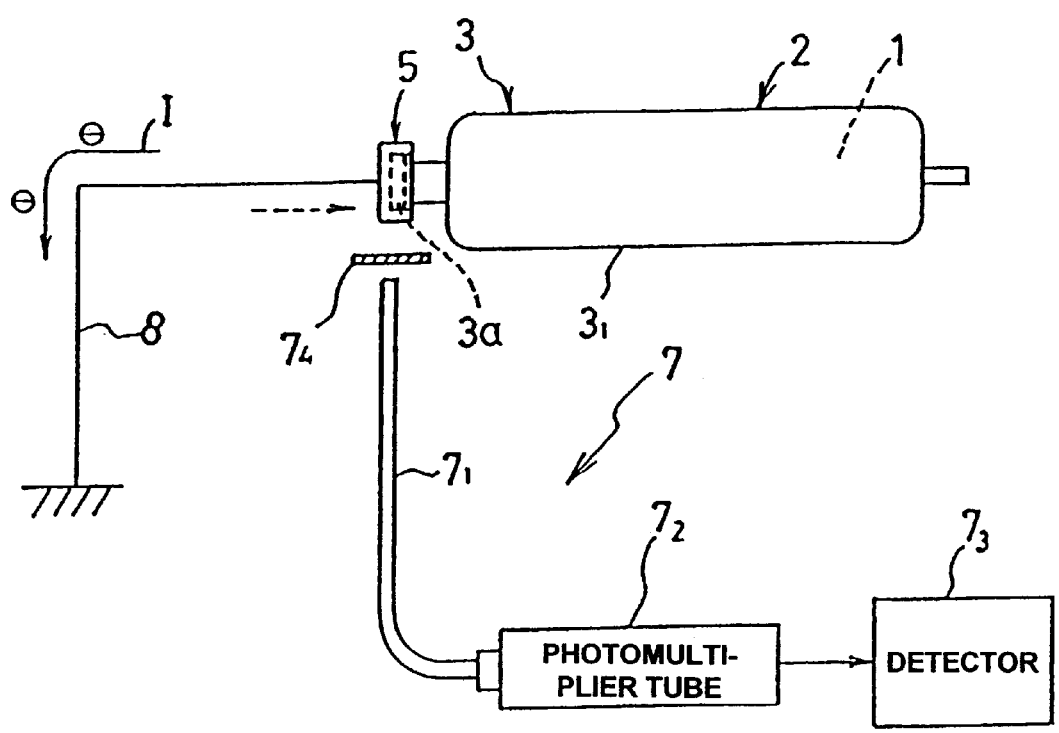

FIG. 2 shows an example in which pinhole inspection is performed by efficiently detecting the occurrence of light emission due to electric discharge that occurs in the presence of a pinhole at the inspection-object portion 3a while the grounded electrode 5 is brought into proximity to or contact with the inspection-object portion after the electrification of the contents 1 of a transfusion bottle of physiological saline or the like in the same way as in Example 1.

In this case, the electrode 5 connected to the grounding wire 8 is put into proximity to the inspection-object portion 3a or the inspection-object portion 3a is fitted into the electrode 5 as in Example 1. An end face of an optical fiber $7_1$ is placed so as to confront the position of occurrence of electric discharge, which would occur in the presence of a pinhole at the inspection-object portion, via an ultraviolet-transmitting, visible-absorption filter $7_4$, while the other end of the optical fiber $7_1$ is connected to a photomultiplier tube $7_2$, and further an output of the photomultiplier tube $7_2$ is inputted to a detector $7_3$. In addition, this optical fiber $7_1$ is given by one which permits easy transmission of ultraviolet rays.

Thus, light emission due to electric discharge in the presence of a pinhole at the inspection-object portion $3a$ has its ultraviolet rays alone inputted to the photomultiplier tube $7_2$ via the optical fiber $7_1$ by the ultraviolet-transmitting, visible-absorption filter $7_4$, and further converted into electricity with high efficiency by the photomultiplier tube $7_2$, thus making it possible to detect light emission due to the discharge with the detector $7_3$. Even if the light emission due to the discharge is weak or if the place is so bright that light is hard to detect, it can easily be detected by using ultraviolet rays that a pinhole is present at the inspection-object portion $3a$.

If no pinhole is present at the inspection-object portion $3a$, there will not occur electric discharge, so that the sensor 7 from the ultraviolet-transmitting, visible-absorption filter $7_4$ to the detector $7_3$ will not be activated. By this fact, it can be detected that no pinhole is present at the inspection-object portion $3a$.

EXAMPLE 3

Figure 3:
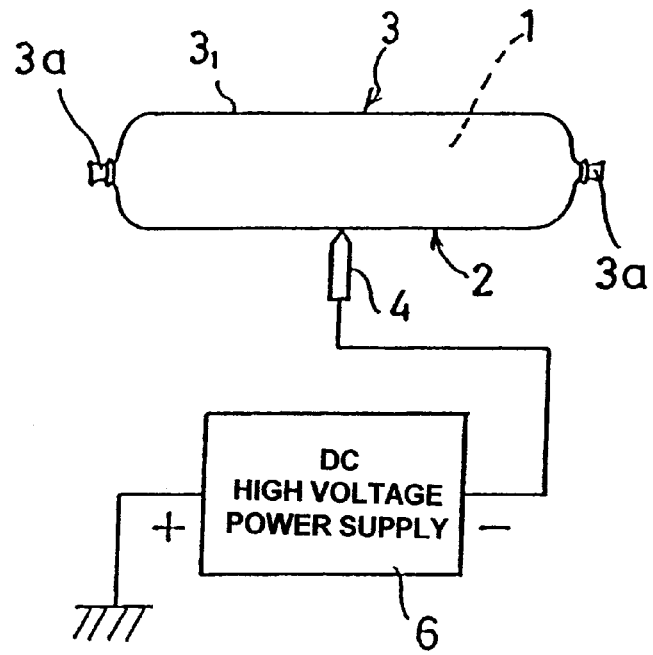
FIG. 3 is an arrangement diagram of electrification of the contents in the case where a sausage or the like with both ends tightly bound is inspected for pinholes.

FIG. 3 shows a case in which the inspection-object portion $3a$ of the hermetically sealed package 3 is a tightly binding portion of a bag in which contents 1 are hermetically sealed. with an electrically insulating film 2, where the electrical conductor 4 derived from the negative-side output terminal of the DC high voltage power supply 6 is put into contact with the side face portion $3_1$ of the inspection object 3 so that the contents 1 are electrified by a high voltage (0.6 kV–30 kV) of the DC high voltage power supply 6. In this case, pinholes which may occur to the electrically insulating film 2 will be concentrated around the inspection-object portion $3a$ at both ends.

The contents 1 are, for example, fish sausage or the like. As the electrically insulating film 2, a single-substance film of vinylidene chloride is used by virtue of its transparency and superior contractibility and barrier property, and the end,portion of the bag which is filled with the contents is tightly bound with aluminum wire.

For detection of pinholes at both-end inspection-object portions $3a, 3a,$ as an electrode 5 connected to the grounded grounding wire 8 as in Example 1 (although not shown, which is an electrode given by a small cup-like metallic member, smaller than that of Example 1, having a recessed portion into which the inspection-object portion $3a$ can be fitted as in Example 1) is brought into proximity to or coverage of the inspection-object portion $3a$ as in Example 1, electric discharge, which occurs in the presence of a pinhole at the inspection-object portion $3a$, is generated and light or/and noise generated due to the discharge is detected by the method shown in Example 1 or Example 2. By this detection, it can be detected that a pinhole is present at the inspection-object portion $3a$.

If no pinhole is present at the inspection-object portion $3a$, there will not occur electric discharge, so that the sensor 7 will not be activated. By this fact, it can be detected that no pinhole is present at the inspection-object portion $3a$.

EXAMPLE 4

Figure 4:
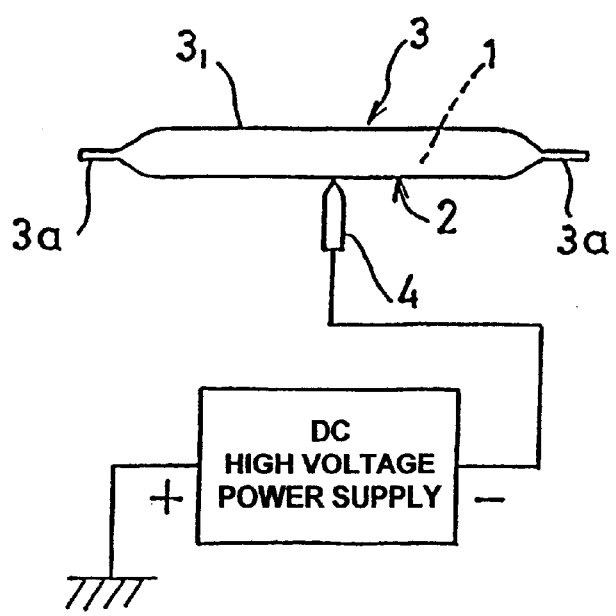
FIG. 4 is an arrangement diagram of electrification of the contents in the case where a food contained in a heat sealed bag such as retort food is inspected for pinholes.

FIG. 4 shows a case where a hermetically sealed package 3, such as retort food (curry, cooked rice, etc.), in which the inspection-object portions $3a, 3a$ are heat sealed portions of a bag made of plastic film is inspected for the presence or absence of pinholes. In such hermetically sealed packages, pinholes which may occur to the electrically insulating film will be concentrated around the inspection-object portions $3a$, which are the heat sealed portions.

The electrically conductive contents 1 are completely cooked food contained in a bag. As the electrically insulating film 2, the aforementioned composite plastic film (laminate film) is used.

For the detection of pinholes at the inspection-object portions $3a, 3a,$ which are the heat sealed portions at both sides of the inspection-object package 3, as in the foregoing Examples 1, 2 and 3, the electrical conductor 4 derived from the negative-side output terminal of the DC high voltage power supply 6 is put into contact with the side face portion $3_1$ of the inspection-object package 3 so that the contents 1 are electrified by a high voltage (0.6 kV–30 kV) of the DC high voltage power supply 6.

After that, as in the foregoing Examples, the electrode 5 connected to the grounded grounding wire 8 (in this case, in correspondence to the individual broad widths of the both-end inspection-object portions $3a$ of the retort-food hermetically sealed package 3, an electrically conductive brush having a broad width corresponding to the aforementioned broad widths and made of electrically conductive plastic fiber is used as the electrode) is brought into proximity to or contact with the inspection-object portion $3a$. As a result of this, electric discharge occurs between the forward end of the brush and the inspection-object portion $3a$ in the presence of a pinhole at the inspection-object portion $3a$, and electric discharge does not occur in the absence of any pinhole at the inspection-object portion $3a$. The electric discharge that occurs in this case is detected by detecting light or/and noise generated due to the discharge by the method shown in Example 1 or Example 2. By this detection, it can be detected that a pinhole is present at the inspection-object portion $3a$.

If no pinhole is present at the inspection-object portions $3a$, there will not occur electric discharge, so that the sensor 7 will not be activated. By this fact, it can be detected that no pinhole is present at the inspection-object portions $3a$, as in the foregoing Example.

EXAMPLE 5

Figure 5A:
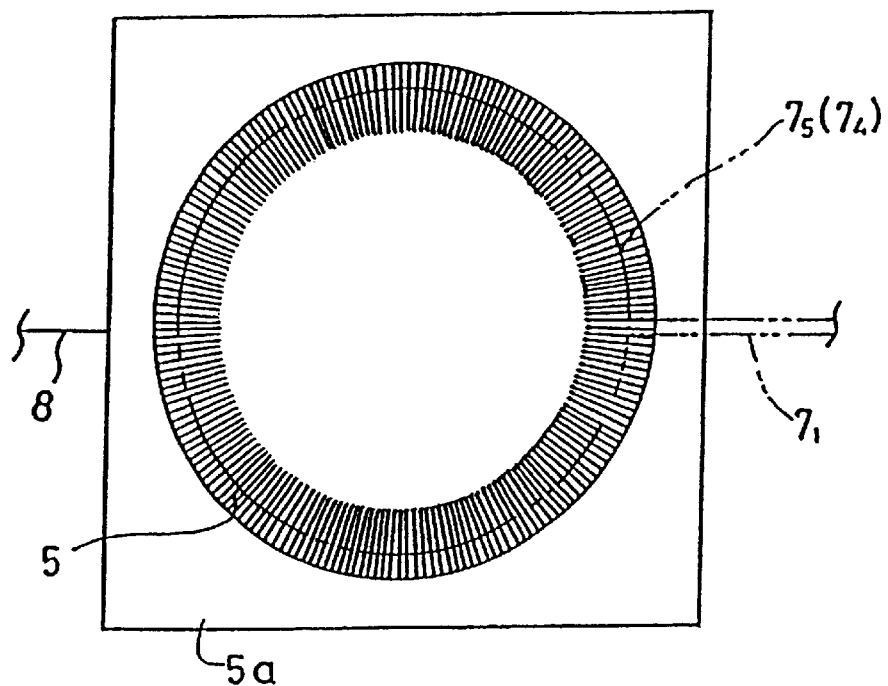
FIG. 5 is an arrangement diagram in the case where the pinhole inspection is performed after the electrification of the contents of a hermetically sealed cup container for pudding, jelly or the like, where FIG. 5 (A) is a plan view showing a positional relationship among a brush electrode, an ultraviolet-transmitting, visible-absorption filter and an ultraviolet-converting fluorescent glass and FIG. 5 (B) is an arrangement diagram showing a state during the inspection.
Figure 5B:
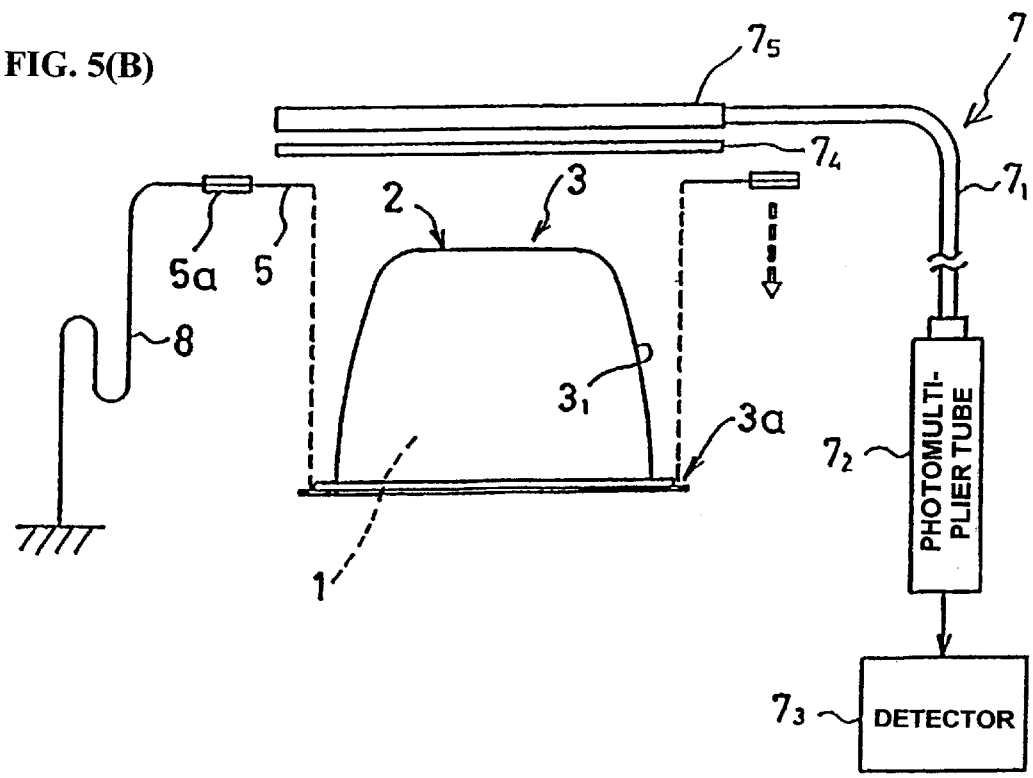

FIG. 5 shows a case in which the presence or absence of pinholes and any seal failure of the hermetically sealed package 3 such as pudding or jelly are detected, where the inspection-object portion $3a$ is an annular heat sealed portion of a hermetically sealed plastic cup container.

On the outer-peripheral edge portion of an opening of the cup formed of a rather thick plastic film 2 having electrically conductive contents 1 such as pudding or jelly contained therein, an annular heat sealed portion is formed by thermally welding and sealing a plastic film of a specified thickness for use of closing the cup opening by means of ultrasonic waves. In such hermetically sealed packages 3, pinholes will be concentrated around the inspection-object portion $3a$, which is the annular heat sealed portion.

For the detection of pinholes at the inspection-object portion $3a$, which is the heat sealed portion of the inspection-object package 3, first, the electrical conductor 4 derived from the negative-side output terminal of the DC high voltage power supply 6 is put into contact with the side face portion $3_1$ of the inspection-object package 3 so that the contents 1 are electrified by a high voltage (0.6 kV–30 kV) of the DC high voltage power supply 6, as in the foregoing Examples.

After that, the electrode 5 connected to the grounded grounding wire 8 is brought into proximity to or contact with the inspection-object portion $3a$, in which state the inspection-object portion $3a$ is inspected for pinholes as in the foregoing Examples. In this case, as the electrode 5, an annular conductive brush electrode 5 is formed, in correspondence to the annular inspection-object portion 3a, which is the annular heat sealed portion of the hermetically sealed package 3, by fixing and holding electrically conductive plastic fiber annularly to a brush holding member made of a metal or an electrically conductive plastic so that the plastic fiber has such a specified inner diameter that its inner end confronts a junction portion between the outer-peripheral edge portion of the cup, which is the inspection-object portion, and a plastic film for closing the cup opening having an outer diameter rather larger than the outer-peripheral edge portion. Then, the electrode 5 is connected to the terminal end of the grounded grounding wire 8, and placed at a specified position upward of the cup-like hermetically sealed package 3 with its bottom upward, where the electrically conductive brush electrode 5 is lowered in the inspection of pinholes of the inspection-object package 3 so that the forward end of the brush confronts the inspection-object portion 3a. Also, the ultraviolet-transmitting, visible-absorption filter $7_4$ is placed upward of the electrically conductive brush electrode 5 with a specified interval thereto, and further an ultraviolet-converting fluorescent glass $7_5$ is placed further upward in proximity to the filter $7_4$, so that light emission due to electric discharge that occurs in the presence of a pinhole at the inspection-object portion 3a between the inspection-object portion 3a, which is the annular heat sealed portion, and the electrically conductive brush electrode 5a is allowed to lend only its ultraviolet components to being incident on the ultraviolet-converting fluorescent glass $7_5$ via the ultraviolet-transmitting, visible-absorption filter $7_4$. Then, out of ultraviolet rays transmitted through the filter $7_4$ by the ultraviolet-converting fluorescent glass $7_5$, fluorescent light is emitted from the fluorescent glass $7_5$, and the light emission is converted into electricity through the optical fiber $7_1$ with high efficiency by the photomultiplier tube $7_2$, where an output thereof is detected by the detector $7_3$.

As a result of this, light emission due to the electric discharge that occurs at the annular inspection-object portion 3a surely causes the ultraviolet-converting fluorescent glass $7_5$ to emit light via the ultraviolet-transmitting, visible-absorption filter $7_4$ no matter where the place of light emission is. Even if the light emission due to the discharge is weak or if it is light in the neighborhood, a pinhole at the inspection-object portion, if any, can easily be detected by detecting the electric discharge reliably and highly efficiently. If no pinhole is present at the inspection-object portion 3a, there will not occur electric discharge, so that the detector $7_3$ will not detect light emission. By this fact, it can be detected that no pinhole is present at the inspection-object portion 3a.

In any of the above examples, since the contents of the inspection-object hermetically sealed package are electrified and then the presence or absence of generation of light or/and noise due to the discharge is detected with a sensor, any pinhole can be detected without errors irrespectively of the atmosphere in the inspection based on the fact that electric discharge will not occur unless pinholes are present at the inspection-object portion.

In the above examples, in the process of electrifying the contents of the inspection-object hermetically sealed package by using the electrical conductor, the electrical conductor is connected to the negative (−) side of the DC high voltage power supply whose positive (+) side is grounded. However, it is needless to say that the electrical conductor may also be connected to the positive (+) side of the DC high voltage power supply whose negative (−) side is grounded, by which the contents are electrified.

Also, when the contents of the inspection-object hermetically sealed package are less electrifiable or when the contents to be electrified are small in quantity, it is also possible to perform the inspection by, while making electrification, putting the electrode connected to the grounded grounding wire into proximity to or contact with the inspection-object portion, simultaneously. Besides, the electrode may be given by those made from electrically conductive rubber or electrically conductive plastic other than metallic electrodes, and further electrically conductive blind electrode made of conductive chains are usable in addition to electrically conductive brushes.

Furthermore, in addition to the aforementioned examples, the method for inspecting hermetically sealed packages according to the present invention can be applied to injection solutions or ampoules of internal medicine in a similar manner. For example, with the main body portion of an ampoule placed on a support member having a circular-arc inner surface, an electrical conductors derived from a DC high voltage power supply is put into contact with or proximity to a side face of the ampoule, making the content solution within the ampoule electrified. After that, a forward end of the electrically conductive brush is brought into proximity to or contact with a forward end portion of the ampoule including its neck portion where pinholes are more likely to occur, which is the inspection-object portion, in which state the presence or absence of light or/and noise due to electric discharge that occurs between the forward end of the brush and the inspection-object portion is detected with a sensor, thus making it possible to inspect pinholes. Like this, the inspection method of the invention lends itself to a wide range of applications.

According to the method for inspecting a hermetically sealed package as described in claim 1 of the present invention, in the pinhole inspection of a hermetically sealed package in which contents such as electrically conductive fluid or powder or food are covered with an electrically conductive film, the contents of the inspection-object hermetically sealed package are electrified with an extremely simple means, and further the presence or absence of generation of light or/and noise due to the electric discharge that occurs between the electrode connected to the grounded grounding wire and the inspection object put into proximity to or contact with the electrode only in the presence of a pinhole is detected by a sensor, by which any pinhole of the hermetically sealed package is detected. With this arrangement, the hermetically sealed package can be inspected for the presence or absence of pinholes effectively with simple means, in combination with the inspection of the inspection-object portion at a site where pinholes are most likely to occur, while fully preventing the occurrence of any misoperations, and without being affected by the atmosphere during the inspection such as humidity or floating fine dusts, as would conventionally be involved in the pinhole detection by the magnitude of the current flowing through the inspection object with a high voltage applied thereto.

According to the invention as described in claim 2, by the use of an electrically conductive brush made of electrically conductive plastic fiber as the electrode for the occurrence of electric discharge between the inspection-object portion and the itself, it becomes easy to form an electrode corresponding to the inspection-object portion, and moreover the electrically conductive brush is so soft as not to damage the inspection object during the inspection.

According to the invention as described in claim 3, the detection of the presence or absence of generation of light due to electric discharge that occurs in the presence of a pinhole at the inspection-object portion is done by letting light emission due to the discharge incident on the photomultiplier tube via the optical fiber to convert the light into electricity by the photomultiplier tube, and detecting the electricity by the detector. With this arrangement, even with a weak light emission due to the discharge, the light emission can easily be detected.

According to the invention as described in claim 4, the light emission due to the electric discharge is let incident on the optical fiber via an ultraviolet-transmitting, visible-absorption filter. With this arrangement, even if the place is so bright that light is hard to detect, the light emission can easily be detected by detecting only ultraviolet rays generated by the discharge phenomenon.

According to the invention as described in claim 5, the light emission due to the electric discharge is let incident on the optical fiber via an ultraviolet-transmitting, visible-absorption filter and an ultraviolet-converting fluorescent glass. With this arrangement, in the case where the inspection-object portion is annular or other shaped and wide in range, by using an ultraviolet-transmitting, visible-absorption filter and an ultraviolet-converting fluorescent glass both of which are so wide as to cover the annular or other shape, it becomes possible to easily capture electric discharge no matter where in the annular or other shape electric discharge has occurred, convert only ultraviolet components of the emitted light into fluorescent light, and thus easily detect the light emission due to the discharge.

What is claimed is:

1. A method for inspecting a hermetically sealed package, comprising the steps of: electrifying a hermetically sealed package (3) in which contents (1) selected from the group consisting of electrically conductive fluid, powder and food are covered with an electrically insulating film (2) by putting only a single electrical conductor (4) connected to a single voltage output terminal of a pair of voltage output terminals of a DC high voltage power supply (6) into contact with or proximity to a side face portion ($3_1$) of the hermetically sealed package (3) so that the contents (1) in the hermetically sealed package (3) are electrified; then, putting an electrode (5) connected to a grounded grounding see (8) into proximity to or contact with an inspection-object portion (3a); and detecting occurrence of light or/and noise due to electric discharge that occurs in a presence of a pinhole at the inspection-object portion (3a) to thereby detect any pinhole of the hermetricaly sealed package (3).

2. The method for inspecting a hermetrically sealed package according to claim 1, wherein the electrode (5) is an electrically conductive brush made of electrically conductive plastic fiber.

3. The method for inspecting a hermitically sealed package according to claim 1 or 2, wherein the step of detecting the presence or absence of generation of light emission due to electric discharge that occurs in the presence of a pinhole at the inspection-objection potion (3a) is a step of letting light emission due to the discharge incident on a photomultiplier tube ($7_2$) via an optical fiberx ($7_1$) to convert the light into electricity by the photomultiplier tube ($7_2$), and detecting the electricity by a detector ($7_3$).

4. The method for inspecting a hermitically sealed package according to claim 3, wherein the light emission due to the electric discharge is let incident on the optical fiber ($7_1$) via an ultraviolet-transmitting, visible-absorption filter ($7_4$).

5. The method far inspecting a hermitically sealed package according to claim 3, wherein the light emission due to the electric discharge is let incident on the optical fiber ($7_1$) via an ultraviolet-transmitting, visible-absorption filter ($7_4$) and an ultraviolet-converting fluorescent glass ($7_5$).

* * * * *